(12) United States Patent
Bae

(10) Patent No.: US 7,645,065 B2
(45) Date of Patent: Jan. 12, 2010

(54) EXPERIMENTAL MIXING DEVICE

(76) Inventor: Suk-Kyu Bae, 32-10, Yangpyung-Dong 3 Ga, Youngdeungpo-Gu, Seoul (KR) 150-103

( * ) Notice: Subject to any disclaimer, the term of this patent is extended or adjusted under 35 U.S.C. 154(b) by 477 days.

(21) Appl. No.: 11/304,303

(22) Filed: Dec. 14, 2005

(65) Prior Publication Data

US 2006/0193198 A1   Aug. 31, 2006

(30) Foreign Application Priority Data

Feb. 25, 2005   (KR) .............. 10-2005-0016017

(51) Int. Cl.
*B01F 11/00* (2006.01)
(52) U.S. Cl. ............... 366/111; 366/128; 366/209; 366/215; 366/216
(58) Field of Classification Search ............... 366/111, 366/112, 128, 208, 209, 211, 216, 219, 237, 366/215
See application file for complete search history.

(56) References Cited

U.S. PATENT DOCUMENTS

| | | | | |
|---|---|---|---|---|
| 507,414 A * | 10/1893 | Cameron et al. | ........... | 366/237 |
| 1,594,227 A * | 7/1926 | Thompson | ........... | 366/211 |
| 2,117,226 A * | 5/1938 | Stewart | ........... | 366/217 |
| 2,281,242 A * | 4/1942 | Kilmer | ........... | 366/208 |
| 2,418,982 A * | 4/1947 | O'Connor | ........... | 366/112 |
| 2,431,872 A * | 12/1947 | Kavula | ........... | 366/114 |
| 2,433,532 A * | 12/1947 | Schultz | ........... | 366/237 |
| 2,576,116 A * | 11/1951 | Hoffman | ........... | 5/600 |
| 2,809,020 A * | 10/1957 | Magee et al. | ........... | 366/208 |
| 3,132,845 A * | 5/1964 | Norty | ........... | 366/118 |
| 3,161,067 A * | 12/1964 | Moller | ........... | 74/42 |
| 3,212,499 A * | 10/1965 | Koreski | ........... | 422/48 |
| 3,224,737 A * | 12/1965 | Becker | ........... | 366/208 |
| 3,310,292 A * | 3/1967 | Moore | ........... | 366/111 |
| 3,396,947 A * | 8/1968 | Heden | ........... | 366/111 |
| 3,601,372 A * | 8/1971 | Harmes | ........... | 366/219 |
| 3,985,307 A * | 10/1976 | Ebbert et al. | ........... | 241/284 |
| 4,109,319 A * | 8/1978 | Brandt | ........... | 366/219 |
| 4,125,335 A * | 11/1978 | Blume et al. | ........... | 366/209 |
| 4,305,668 A * | 12/1981 | Bilbrey | ........... | 366/111 |
| 4,702,610 A | 10/1987 | Reynolds, Jr. | | |
| 4,893,938 A * | 1/1990 | Anderson | ........... | 366/208 |
| 5,358,265 A * | 10/1994 | Yaple | ........... | 280/293 |
| 5,423,603 A * | 6/1995 | Reynolds et al. | ........... | 366/208 |
| 5,564,826 A * | 10/1996 | Neumann et al. | ........... | 366/219 |
| 5,655,836 A * | 8/1997 | Preston et al. | ........... | 366/208 |

(Continued)

FOREIGN PATENT DOCUMENTS

GB   2243089 A * 10/1991

(Continued)

*Primary Examiner*—David L Sorkin
*Assistant Examiner*—Andrew Janca
(74) *Attorney, Agent, or Firm*—Jordan and Hamburg LLP

(57) ABSTRACT

An experimental mixing device may comprise a driving source, an eccentric member, a control member and a mixing member. The control member may be selective installed in the experimental mixing device and be configured to adjust the mixing member, thereby providing various operational motions of the mixing member, for example an orbital motion, a see-saw motion, a 3-D twist motion, or a crank motion. The use of the control member may eliminate the need of separating the mixing member from the experimental mixing device. Thereby, the experimental mixing device may have adjustable patterns and quantity of the mixing motion and lead to easy usage and manufacture.

3 Claims, 20 Drawing Sheets

U.S. PATENT DOCUMENTS

| | | |
|---|---|---|
| 5,921,676 A | 7/1999 | Reynolds, Jr. |
| 6,148,688 A * | 11/2000 | Nishimaki .................... 74/493 |
| 6,322,243 B1 * | 11/2001 | Bull .......................... 366/208 |
| 6,360,904 B1 * | 3/2002 | Schilb et al. ................ 211/187 |
| 6,680,818 B1 * | 1/2004 | Morita et al. ................ 360/132 |
| 7,296,923 B1 * | 11/2007 | Malasky et al. ............. 366/208 |
| 7,524,104 B2 * | 4/2009 | Malasky et al. ............. 366/208 |
| 2004/0181901 A1 * | 9/2004 | Magoto et al. ................. 16/19 |

FOREIGN PATENT DOCUMENTS

| | | | |
|---|---|---|---|
| JP | 55106531 A | * | 8/1980 |
| WO | WO 99/50021 | * | 7/1999 |

* cited by examiner

EXPERIMENTAL MIXING DEVICE

BACKGROUND OF THE INVENTION

1. Field of the Invention

The present invention relates generally to experimental mixing devices.

2. Description of the Related Art

Generally, an experimental mixing device as a kind of physical and chemical apparatus is used in diluting, agitating or mixing test materials, for example reagent, sample or raw material in testers, for example test tubes or beakers, in laboratory environment.

Several devices have been on the market such as U.S. Pat. Nos. 4,702,610 and 5,921,676.

The prior arts lack in function for adjusting the eccentric distance or the swing angle. Although several devices have a member for adjusting the eccentric distance, they have the inconvenience of separating a portion of components from a mixing device. Users may be unfamiliar with the usage of the mixing devices and thus may use the mixing devices without adjusting the eccentric distance.

SUMMARY OF THE INVENTION

An example embodiment of the present invention is directed to providing an experimental mixing device which may selectively adjust the mixing motion without separation of a mixing member.

Another example embodiment of the present invention is directed to providing an experimental mixing device which may adjust the pattern or quantity of the mixing motion corresponding to experimental requirements.

According to an example embodiment of the present invention, an experimental mixing device may comprise a driving source including a driving motor having a driving axle. An eccentric member may be connected to the driving source and have an eccentric axle formed eccentric with an axial center of the driving axle. A control member may be selectively installed in the experimental mixing device and configured to adjust the eccentric axle. A mixing member may be configured to mix test materials. A support member may be provided below the mixing member and configured to support the mixing member. A base may be provided below the support member and configured to enclose the driving source.

BRIEF DESCRIPTION OF THE DRAWINGS

The example embodiments of the present invention will be readily understood with reference to the following detailed description thereof provided in conjunction with the accompanying drawings, wherein like reference numerals designate like structural elements.

Figure 1:
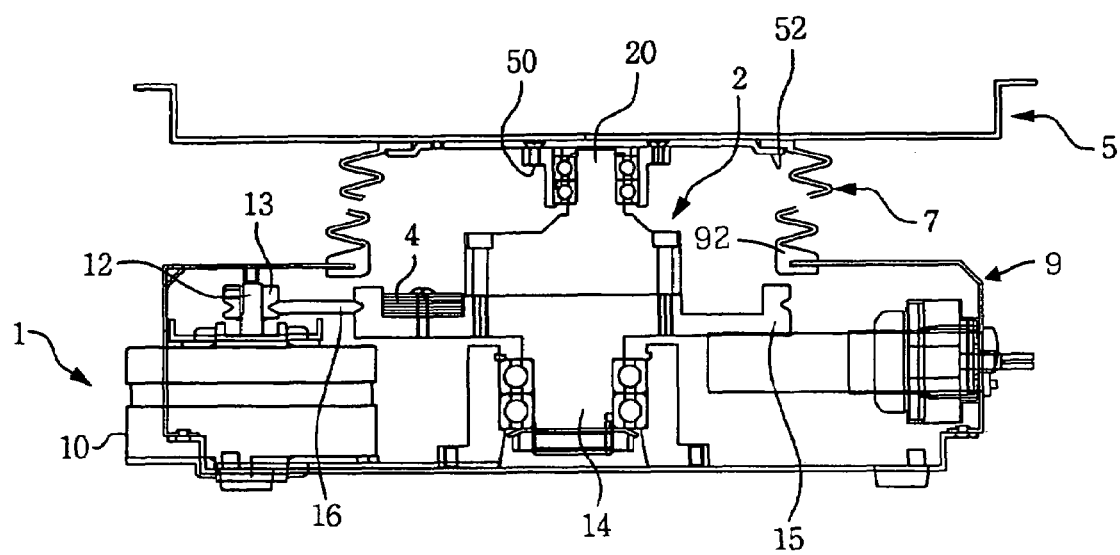
FIG. 1 is a longitudinally cross-sectional view of an experimental mixing device in accordance with an example embodiment of the present invention.

These drawings are provided for illustrative purposes only and are not drawn to scale. The spatial relationships and relative sizing of the elements illustrated in the various embodiments may have been reduced, expanded or rearranged to improve the clarity of the figure with respect to the corresponding description. The figures, therefore, should not be interpreted as accurately reflecting the relative sizing or positioning of the corresponding structural elements that could be encompassed by an actual device manufactured according to the example embodiments of the invention.

DETAILED DESCRIPTION OF THE INVENTION

Example, non-limiting embodiments of the present invention will now be described more fully hereinafter with reference to the accompanying drawings. This invention may, however, be embodied in many different forms and should not be construed as limited to the example embodiments set forth herein. Rather, the disclosed embodiments are provided so that this disclosure will be thorough and complete, and will fully convey the scope of the invention to those skilled in the art. The principles and feature of this invention may be employed in varied and numerous embodiments without departing from the scope of the invention.

It should be noted that the figures are intended to illustrate the general characteristics of methods and devices of example embodiments of this invention, for the purpose of the description of such example embodiments herein. These drawings are not, however, to scale and may not precisely reflect the characteristics of any given embodiment, and should not be interpreted as defining or limiting the range of values or properties of example embodiments within the scope of this invention. Rather, for simplicity and clarity of illustration, the dimensions of some of the elements are exaggerated relative to other elements.

Further, well-known structures and processes are not described or illustrated in detail to avoid obscuring the present invention. Like reference numerals are used for like and corresponding parts of the various drawings.

Figure 2:
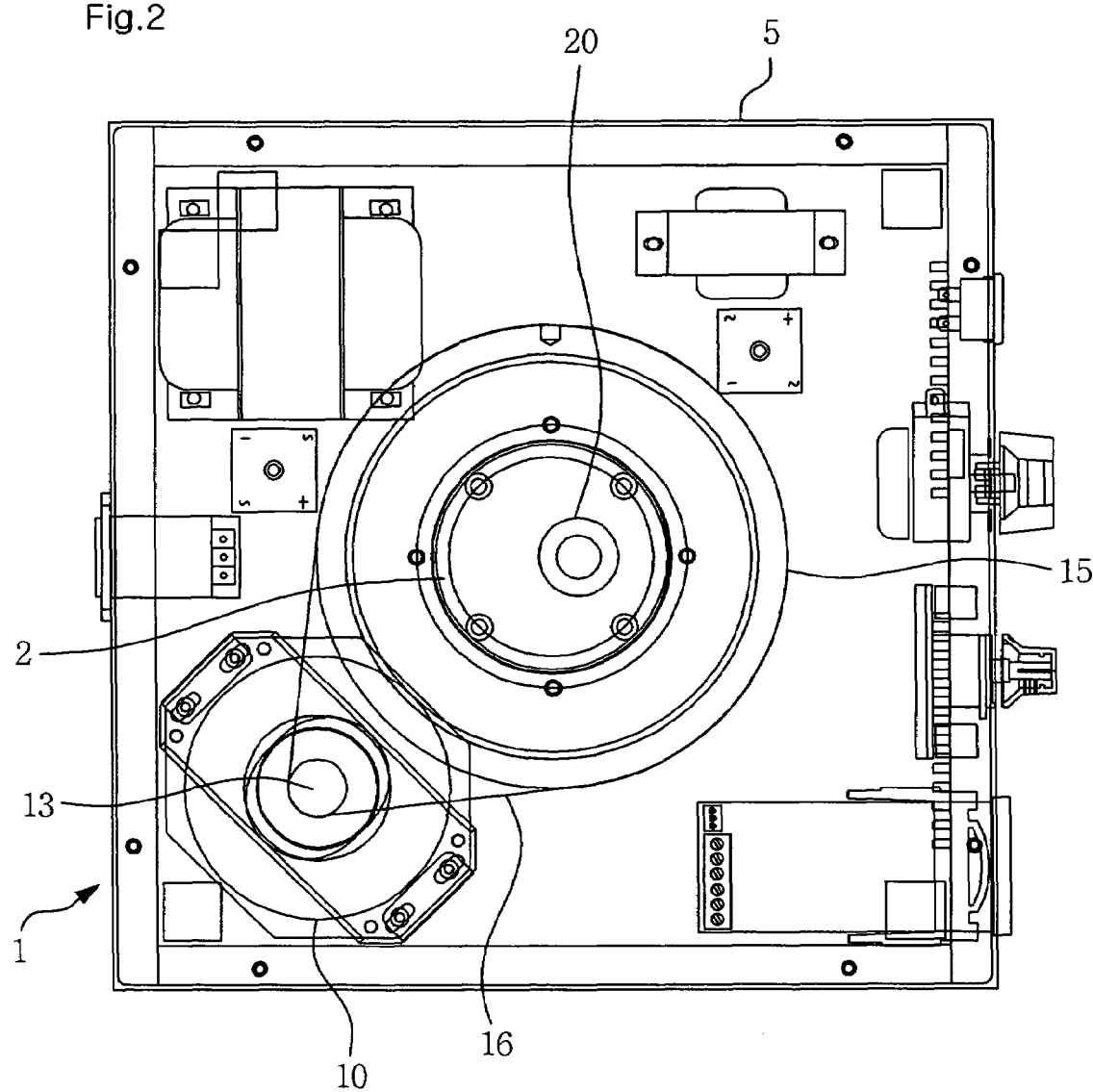
FIG. 2 is a partial plan view of FIG. 1.

FIG. 1 is a longitudinally cross-sectional view of an experimental mixing device in accordance with an example embodiment of the present invention. FIG. 2 is a partial plan view of FIG. 1.

Referring to FIGS. 1 and 2, an experimental mixing device may comprise a driving source 1 including a driving motor 10 having a driving axle 12. An eccentric member 2 may be connected to the driving source 10 and have an eccentric axle 20 formed eccentric with an axial center of the driving axle 12. A mixing member 5 may be configured to mix test materials. A support member 7 may be provided below the mixing member 5 and be configured to support the mixing member 5. A base 9 may be provided below the support member 7 and be configured to enclose the driving source 1.

Specifically, the driving motor 10 of the driving source 1 may have a driving axle 12. A driving pulley 13 may be provided in the driving axle 12. A secondary axle 14 may be provided at the bottom of the eccentric member 2, spaced apart from the driving axle 12, and may be rotatable. A secondary pulley 15 may be provided in secondary axle 14. A belt 16 may connect the driving pulley 13 to the secondary pulley 15 and be configured to transmit power. The eccentric member 2 may be connected to the secondary pulley 15. The eccentric axle 20 may be eccentric with the secondary axle 14. In this example embodiment, the secondary axle 14 may be directly fixed to the eccentric member 2 without a control member. The mixing member 5 may be formed of a table and have an axle support 50 provided on the central bottom thereof. The axle support 50 may receive the eccentric axle 20. A first fastener 52 may be provided on the bottom of the mixing member 5. A second fastener 92 may be provided on the base 9. The support member 7 may be provided between the first fastener 52 and the second fastener 92, and be formed of an elastic undulated member of flexible materials. As the eccentric axle 20 of the eccentric member 2 may be eccentrically rotated by the driving source 1, the mixing member 5 may make a two-dimensional orbital motion.

Figure 3:
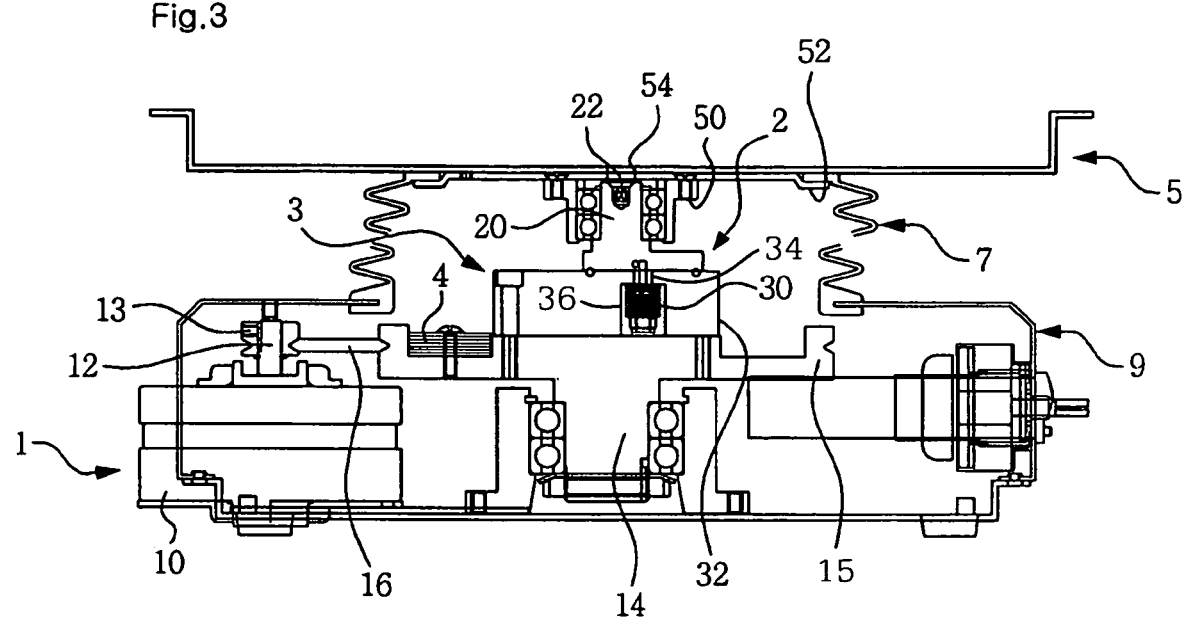
FIG. 3 is a longitudinally cross-sectional view of an experimental mixing device in accordance with another embodiment of the present invention.

FIG. 3 is a longitudinally cross-sectional view of an experimental mixing device in accordance with another embodiment of the present invention.

Referring to FIG. 3, the mixing device may further comprise a control member 3. A driving source, a support member and a base of this example embodiment may be the same as the above example embodiment, and an eccentric member and a mixing member of this example embodiment may be modifications of the above example embodiment. The detailed description of the same components is omitted.

The control member 3 may be configured to control the eccentric distance of the eccentric axle 20, i.e., the distance between the axial center of the secondary axle 14 and the axial center of the eccentric axle 20 to adjust the diameter of an orbital motion.

Specifically, the control member 3 may have an arm 32 and a control eccentric axle 30. The arm 32 may be provided on the secondary pulley 15. The eccentric member 2 may be provided on the arm 32 and be rotated relative to the control eccentric axle 30. The mixing member 5 may have an opening 54 receiving the top of the eccentric axle 20. The eccentric axle 20 may have a multilateral groove 22 formed on the top thereof.

The control eccentric axle 30 may be provided on the bottom of the eccentric member 2 and be located eccentric with the eccentric axle 20. The arm 32 may have an installation hole 34 and 36, which may be eccentric with the secondary axle 14. The installation hole 34 and 36 may penetrate the arm 32 and include an upper portion 34 on the top surface and a lower portion 36 on the bottom surface. The control eccentric axle 30 may be inserted in the upper portion 34 of the installation hole and be protruded from the lower portion 36 of the installation hole. The protruded portion of the control eccentric axle 30 may be joined with a spring 38 and a nut 40.

A plurality of stopper grooves 42 may be radially formed on the bottom surface of the eccentric member 2. A plurality of stopper protrusions 44 may be formed on the top surface of the arm 32, corresponding to the stopper grooves 42.

The stopper protrusions 44 and the stopper grooves 42 may change the position of the eccentric axle 20, thereby adjusting the eccentric distance of the eccentric axle 20. Various methods other than the engagement of the stopper protrusions 44 and the stopper grooves 42 may be used in adjusting the eccentric distance of the eccentric axle 20.

A stopper member 6 may be provided between the driving source 1 and the base 9 and be configured to prevent the rotation of the secondary axle 14 with the rotation of the eccentric axle 20. For example, a plurality of slots 15a may be formed in the secondary pulley 15. A bracket 94 may be formed at one side of the base 9. A knob 90 may be provided in the bracket 94 and be supported by a spring 96. When pressure may be applied to the knob 90, the knob 90 may be inserted in the slot 15a. Thereby the secondary axle 14 may be fixed.

Figure 6:
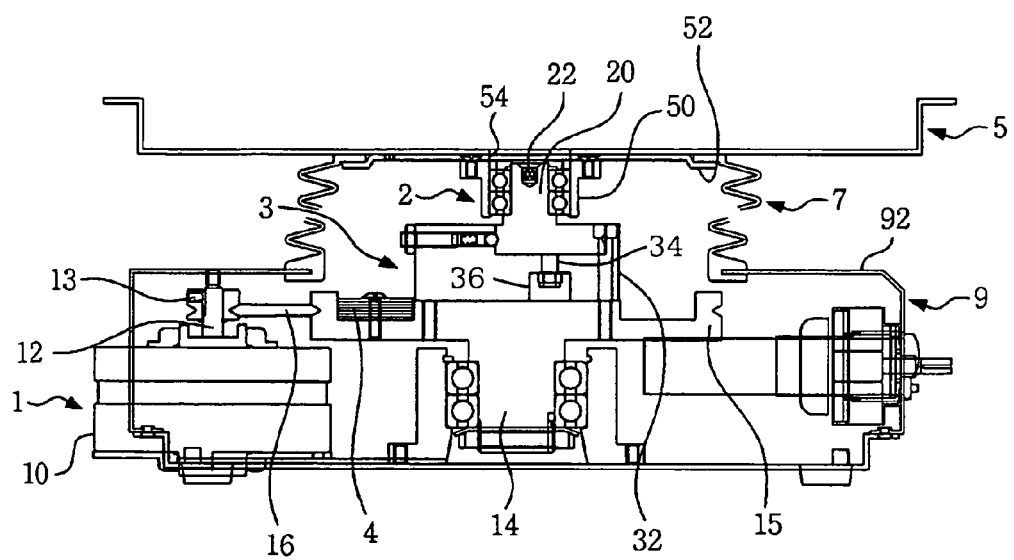
FIG. 6 is a longitudinally cross-sectional view of an experimental mixing device in accordance with another embodiment of the present invention.
Figure 7:
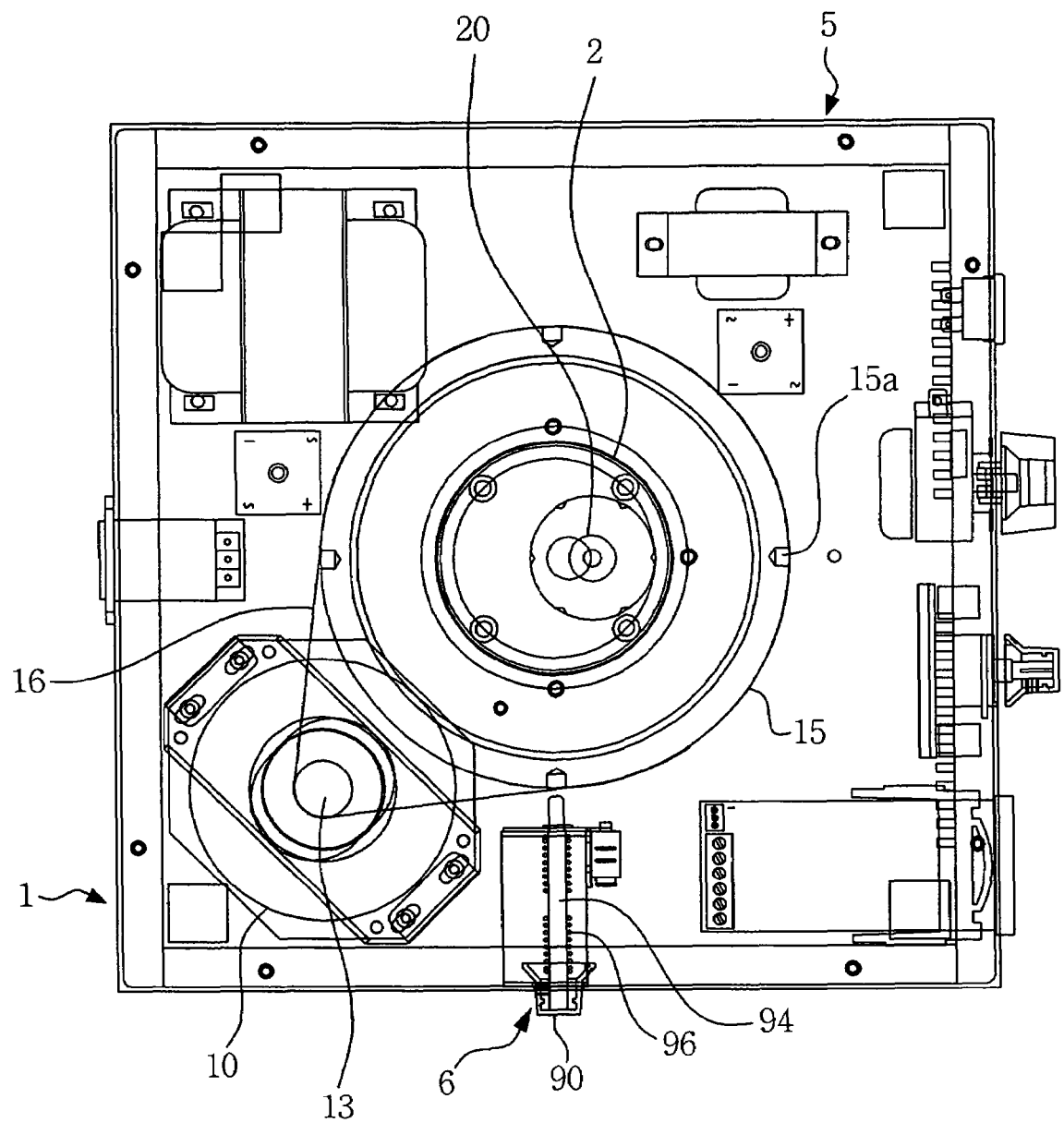
FIG. 7 is a partial plan view of FIG. 6.
Figure 8:
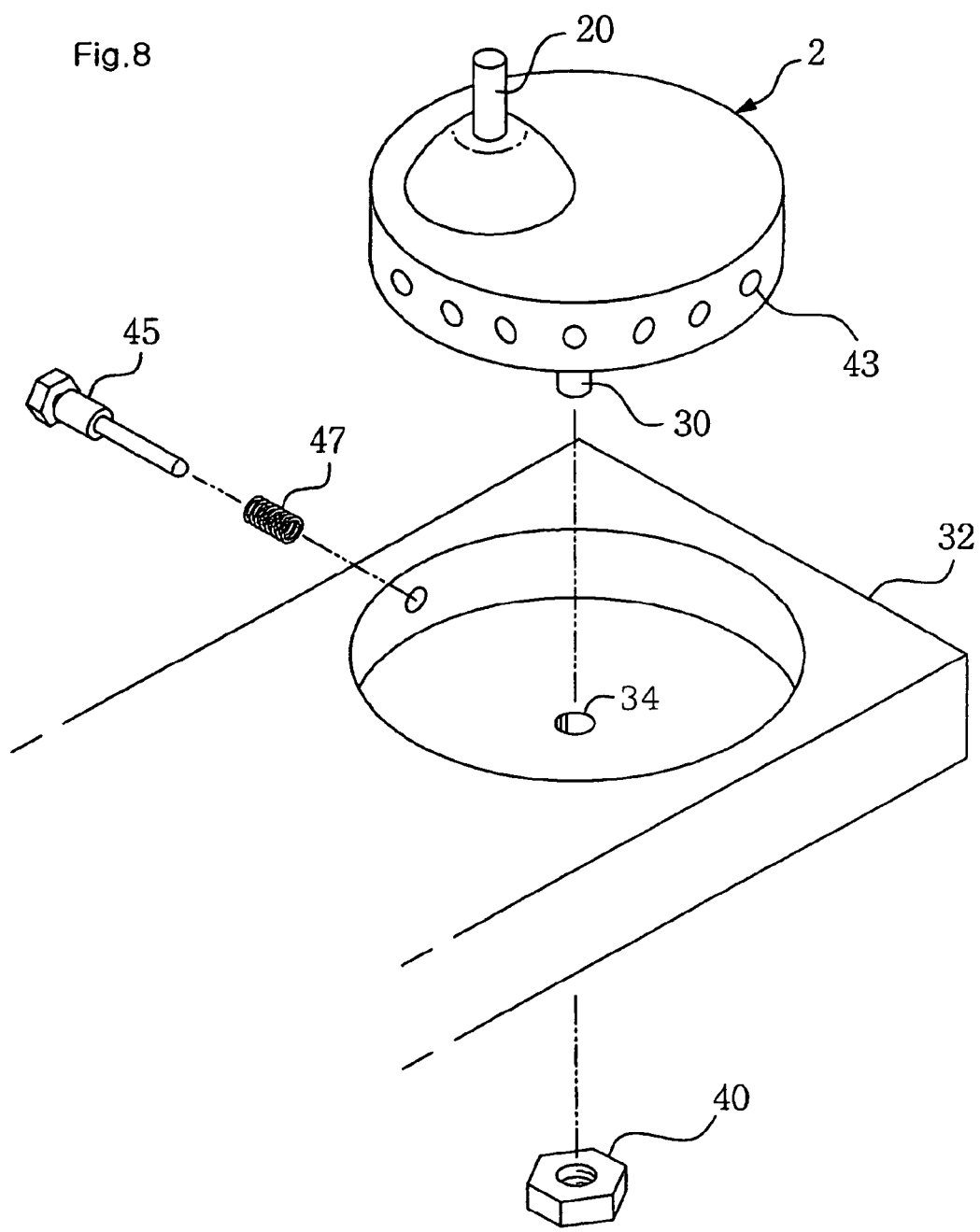
FIG. 8 is an exploded perspective view of an essential part of an experimental mixing device of FIGS. 6 and 7.

FIG. 6 is a longitudinally cross-sectional view of an experimental mixing device in accordance with another embodiment of the present invention. FIG. 7 is a partial plan view of FIG. 6. FIG. 8 is an exploded perspective view of an essential part of a mixing device of FIGS. 6 and 7.

Figure 4:
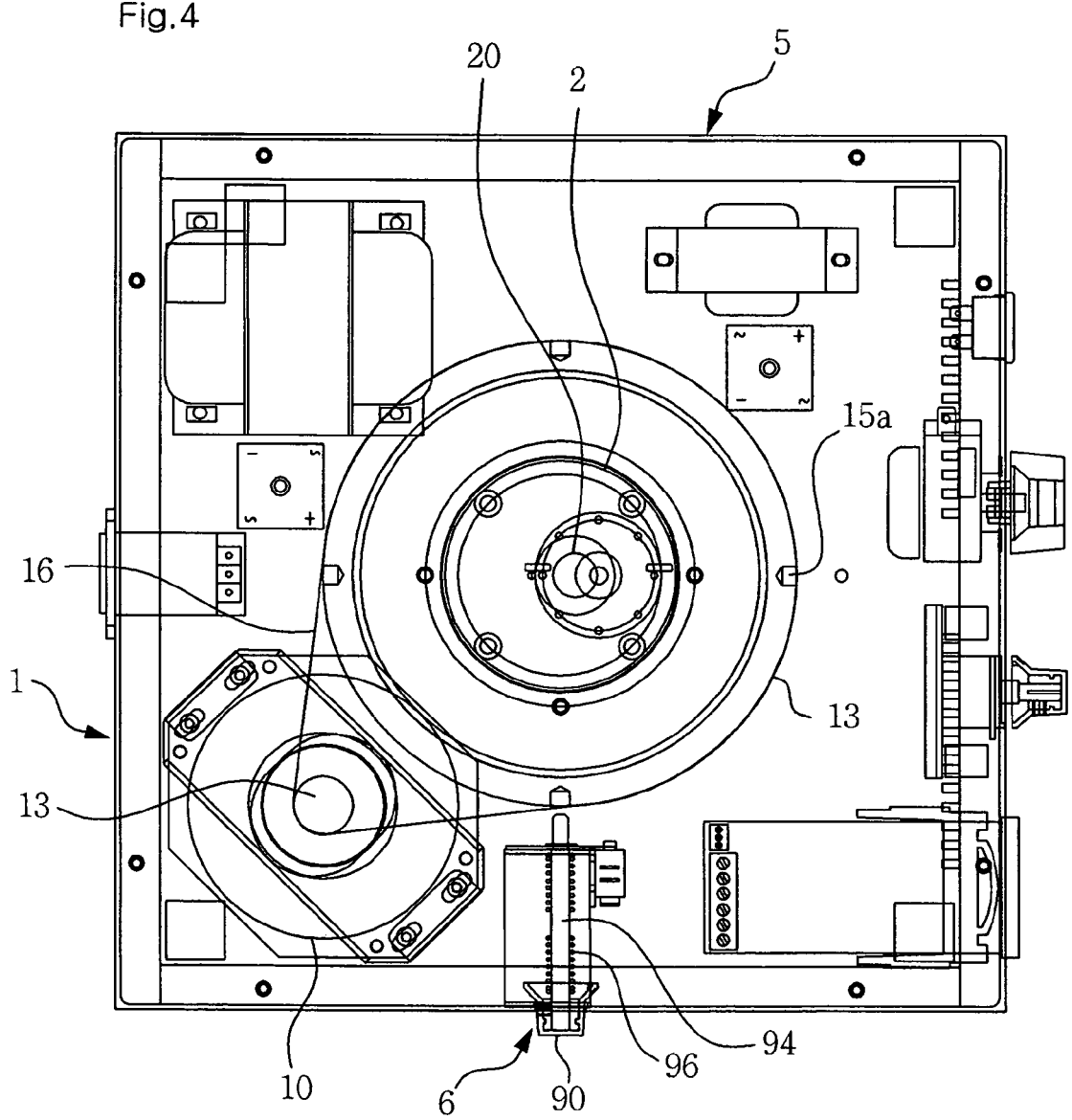
FIG. 4 is a partial plan view of FIG. 3.
Figure 5:
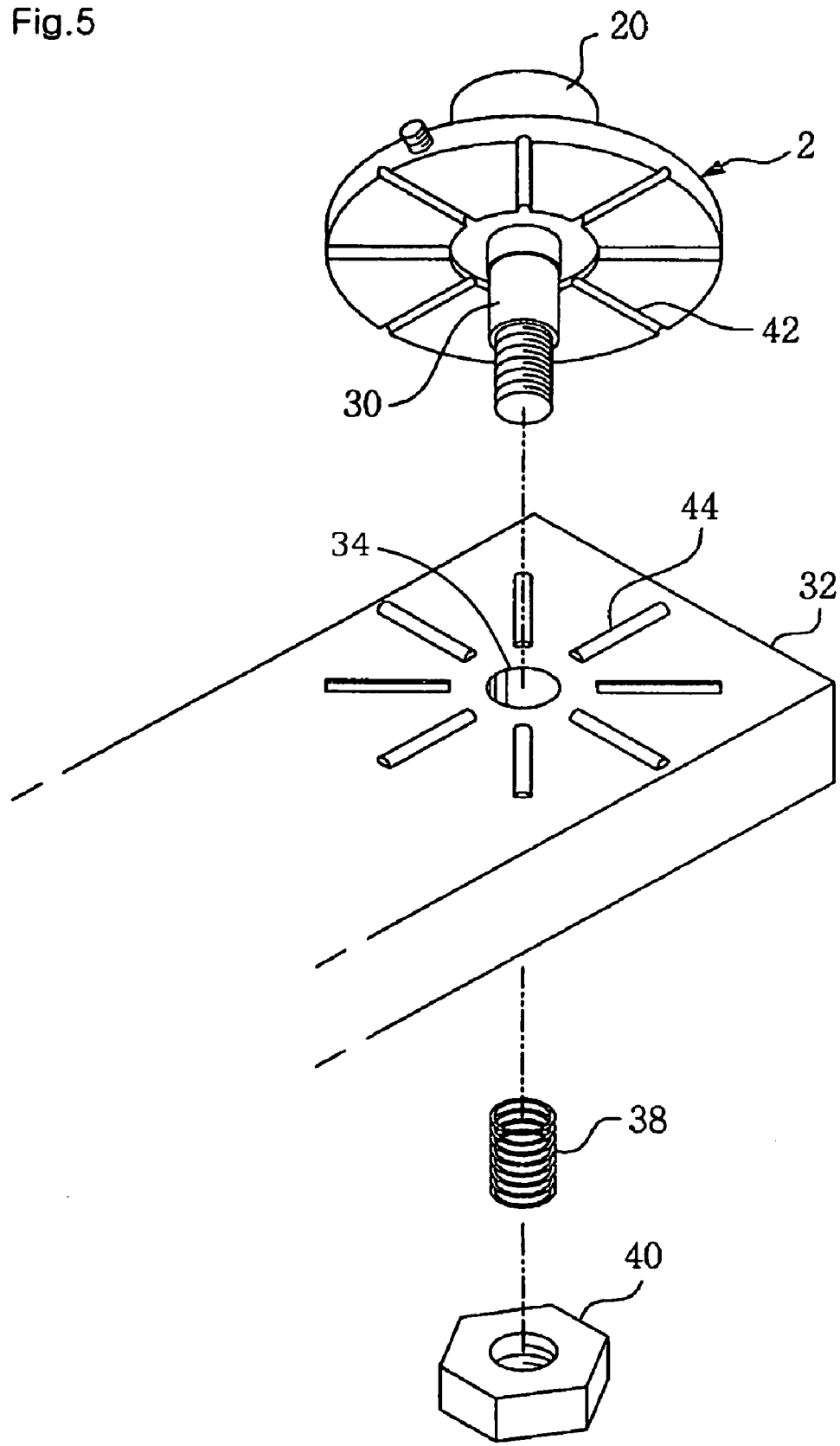
FIG. 5 is an exploded perspective view of an essential part of an experimental mixing device of FIGS. 3 and 4.

Referring to FIGS. 6 through 8, the mixing device of this example embodiment may have the same structure as the mixing device of FIGS. 3 through 5, except for the structure for adjusting an eccentric axle. The detailed description of the same structure is omitted.

An eccentric member 2 may be formed of a cylinder and have a plurality of stopper grooves 43 along the periphery. A stopper 45 may be provided at one side of an arm 32 corresponding to the stopper groove 43 and be supported by a spring 47. The arm 32 may have a recess 46 receiving the eccentric member 2, and an installation hole 34 and 36. The installation hole 34 and 36 may penetrate the arm 32 and include an upper portion 34 on the top surface and a lower portion 36 on the bottom surface. A control eccentric axle 30 may be inserted in the upper portion 34 of the installation hole and be protruded from the lower portion 36 of the installation hole. The protruded portion of the control eccentric axle 30 may be joined with a nut 40. As an eccentric axle 20 may be rotated, the eccentric member 2 may be rotated relative to a control eccentric axle 30. The eccentric member 2 may be fixed at a desired position using the stopper 45 and the stopper groove 43.

Figure 9A:
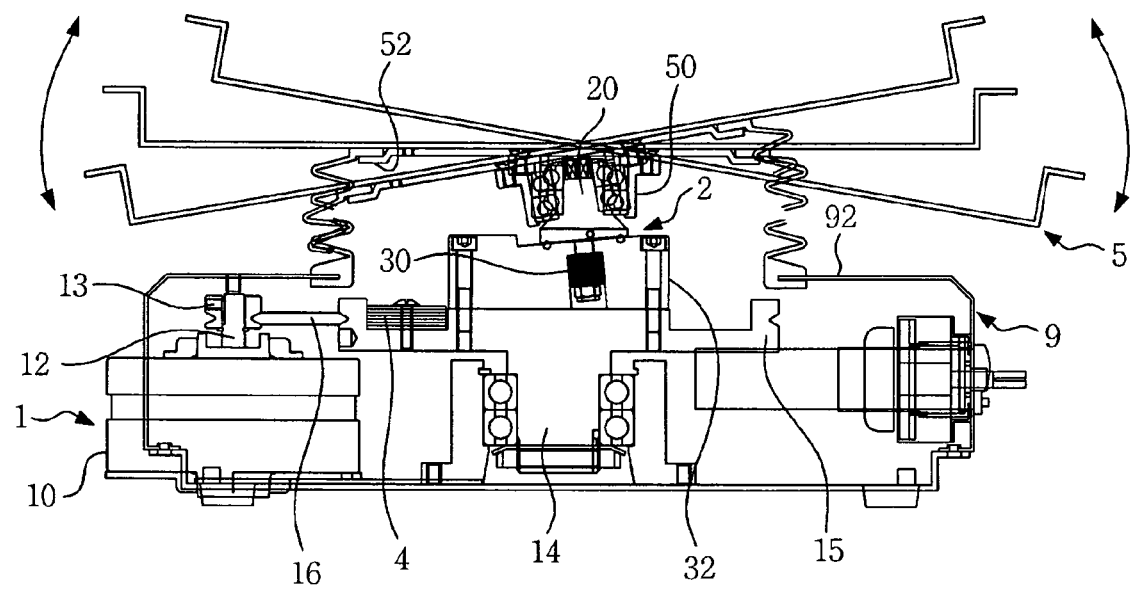
FIG. 9A is a longitudinally cross-sectional view of an experimental mixing device in accordance with another embodiment of the present invention.
Figure 9B:
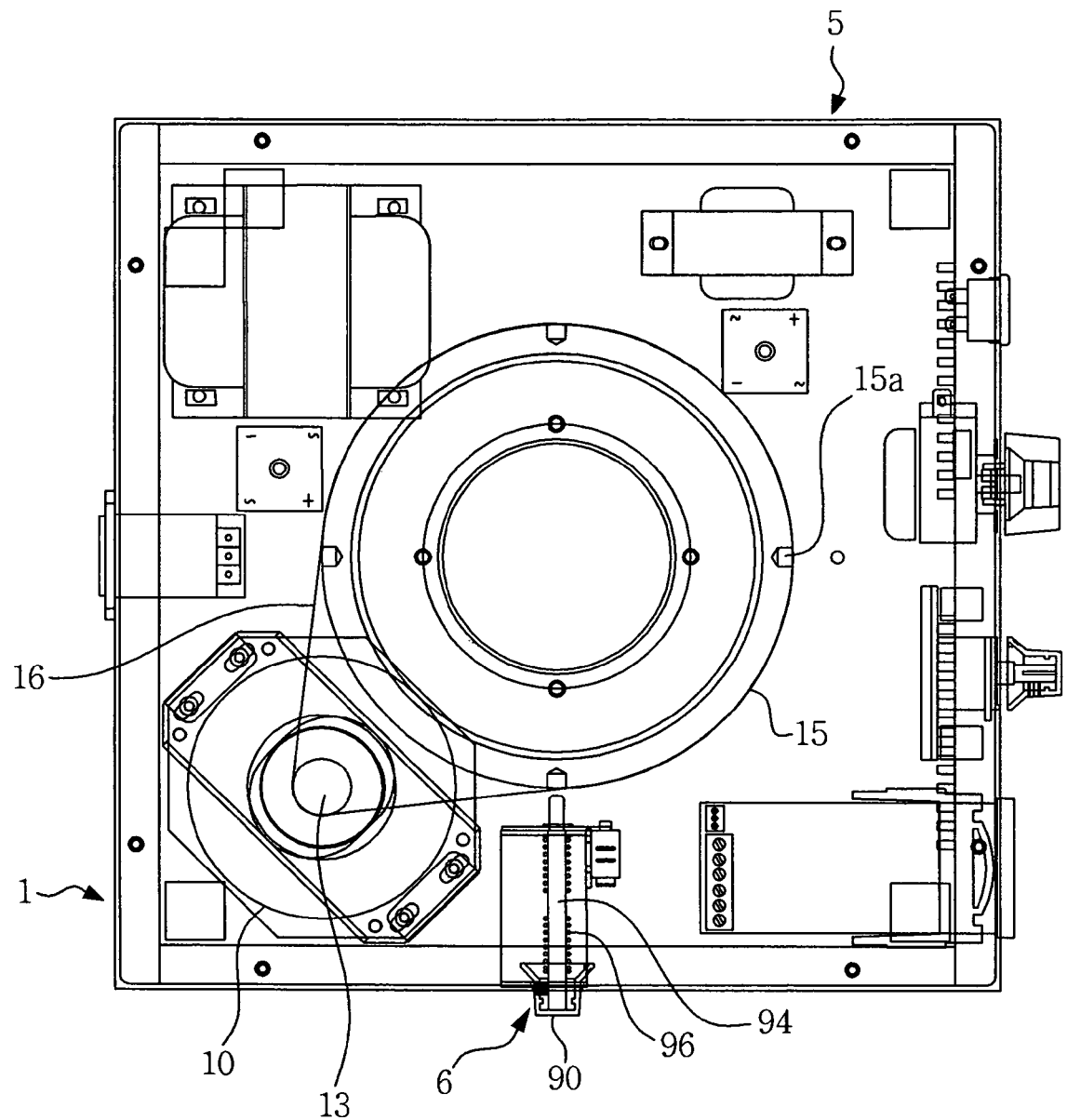
FIG. 9B is a partial plan view of FIG. 9A.

FIG. 9A is a longitudinally cross-sectional view of an experimental mixing device in accordance with another embodiment of the present invention. FIG. 9B is a partial plan view of FIG. 9A. The mixing device of this example embodiment may be a modification of the mixing device of FIGS. 3 through 5.

Referring to FIGS. 9A and 9B, an arm 32 may have the top surface formed tilted so that an eccentric member 2 may be rotated relative to a control eccentric axle 30 at its original position. Thereby the eccentric distance and the tilt angle of the eccentric axle 20 may be simultaneously adjusted to provide a three-dimensional twist motion. If the eccentric member 2 may be adjusted to a horizontal position, two-dimensional horizontal orbital motion may be selectively provided.

Figure 10A:
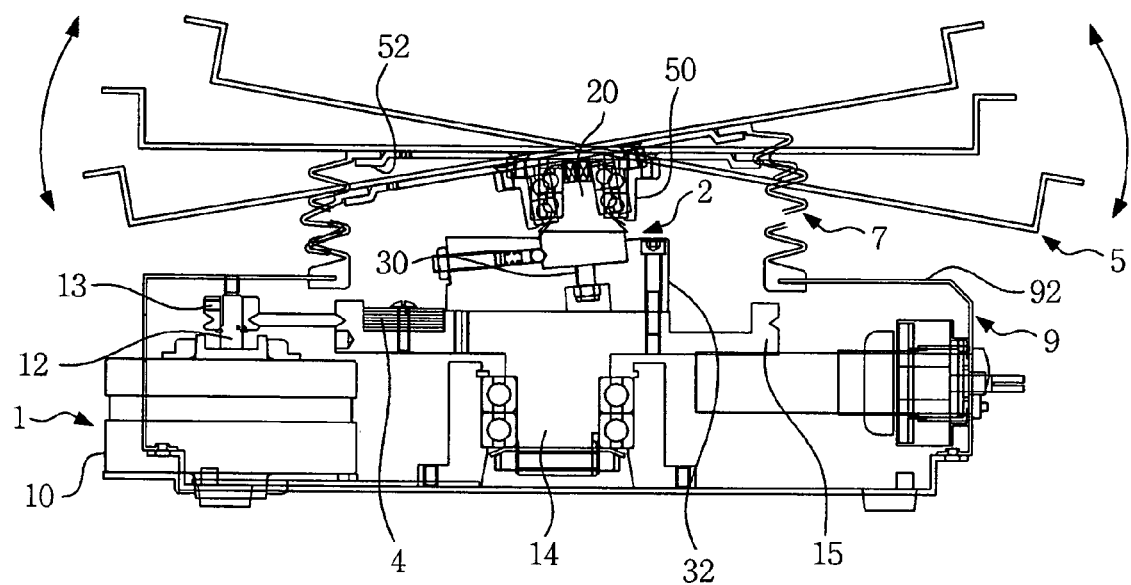
FIG. 10A is a longitudinally cross-sectional view of an experimental mixing device in accordance with another embodiment of the present invention.
Figure 10B:
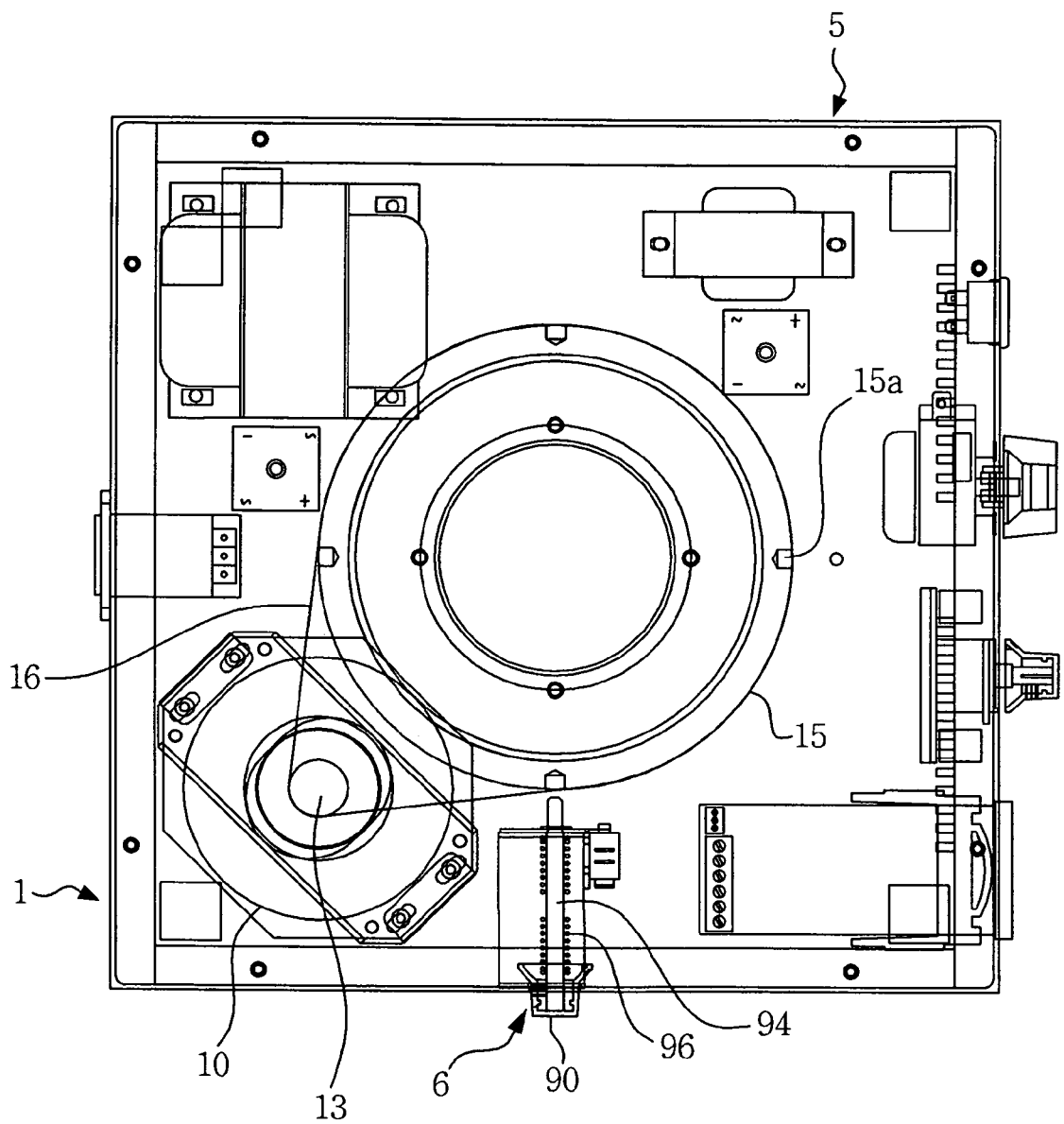
FIG. 10B is a partial plan view of FIG. 10A.

FIG. 10A is a longitudinally cross-sectional view of an experimental mixing device in accordance with another embodiment of the present invention. FIG. 10B is a partial plan view of FIG. 10A. The mixing device of this example embodiment may be a modification of the mixing device of FIGS. 6 through 8.

Referring to FIGS. 10A and 10B, a recess 46 of an arm 32 may have the top surface formed tilted so that an eccentric member 2 may be rotated relative to a control eccentric axle 32 at its original position. The eccentric distance and the tilt angle of the eccentric axle 20 may be simultaneously adjusted to provide a three-dimensional twist motion. If the eccentric member 2 may be adjusted to a horizontal position, two-dimensional horizontal ortibal motion may be selectively provided.

Figure 11A:
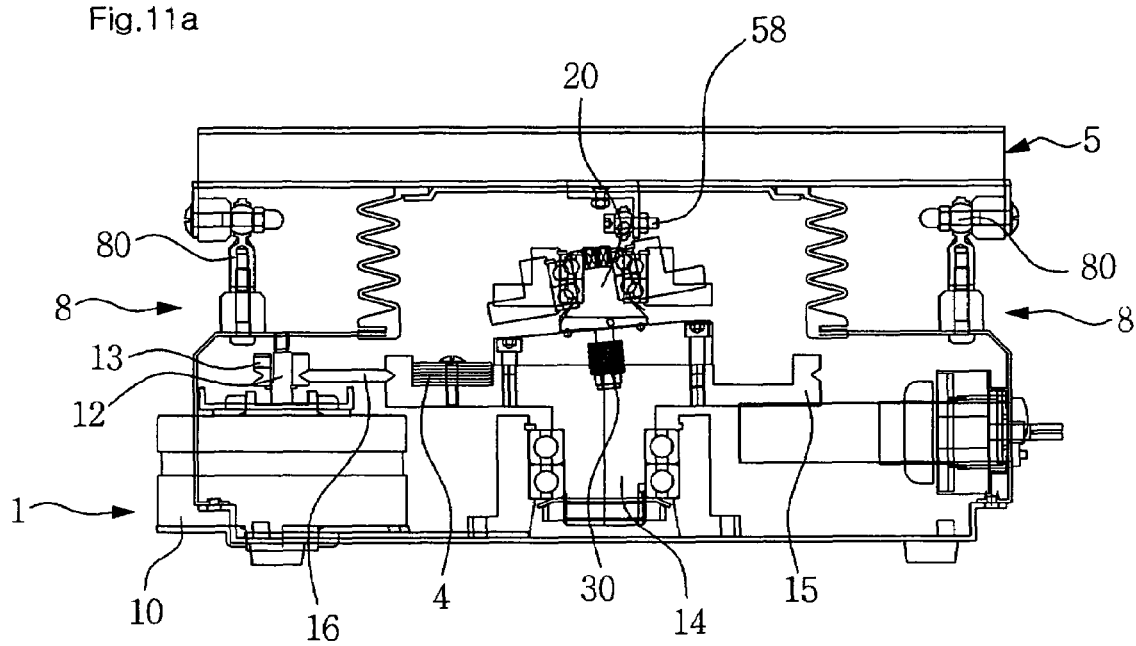
FIG. 11A is a longitudinally cross-sectional view of an experimental mixing device in accordance with another embodiment of the present invention.
Figure 11B:
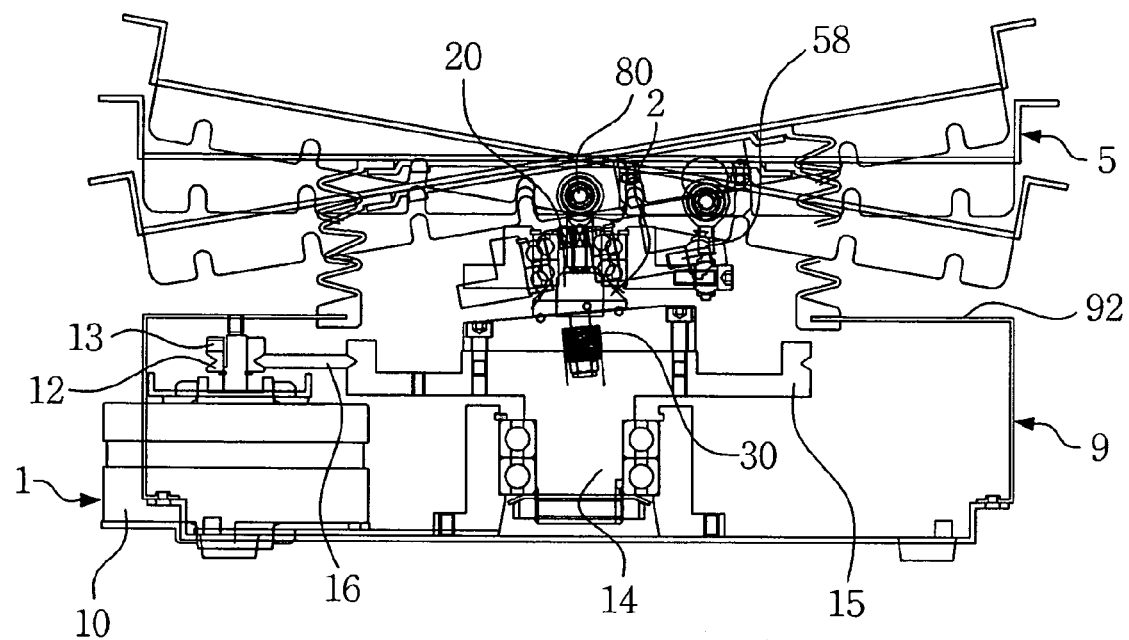
FIG. 11B is a partial side view of FIG. 11A.
Figure 11C:
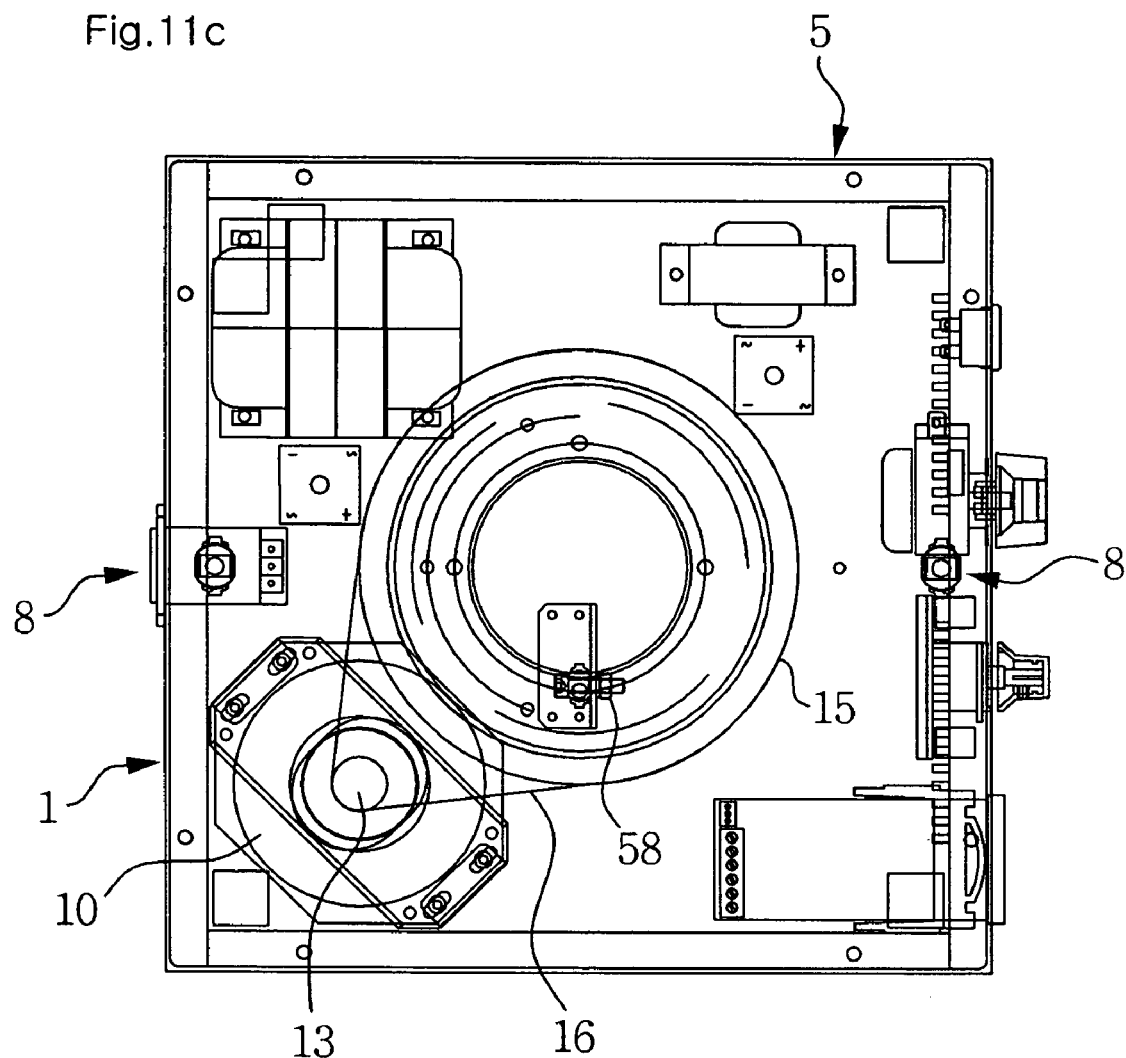
FIG. 11C is a partial plan view of FIG. 11A.

FIG. 11A is a longitudinally cross-sectional view of an experimental mixing device in accordance with another embodiment of the present invention. FIG. 11B is a partial side view of FIG. 11A. FIG. 11C is a partial plan view of FIG. 11A.

Referring to FIGS. 11A through 11C, the mixing device may further comprise a connecting element 58 and a connection member 8. The connection member 8 may have hinged portions 80 arranged at the bottom ends of a mixing member 5 corresponding a base 9. The connection member 8 and the connecting element 58 may allow a see-saw motion of the mixing member 5.

Figure 12:
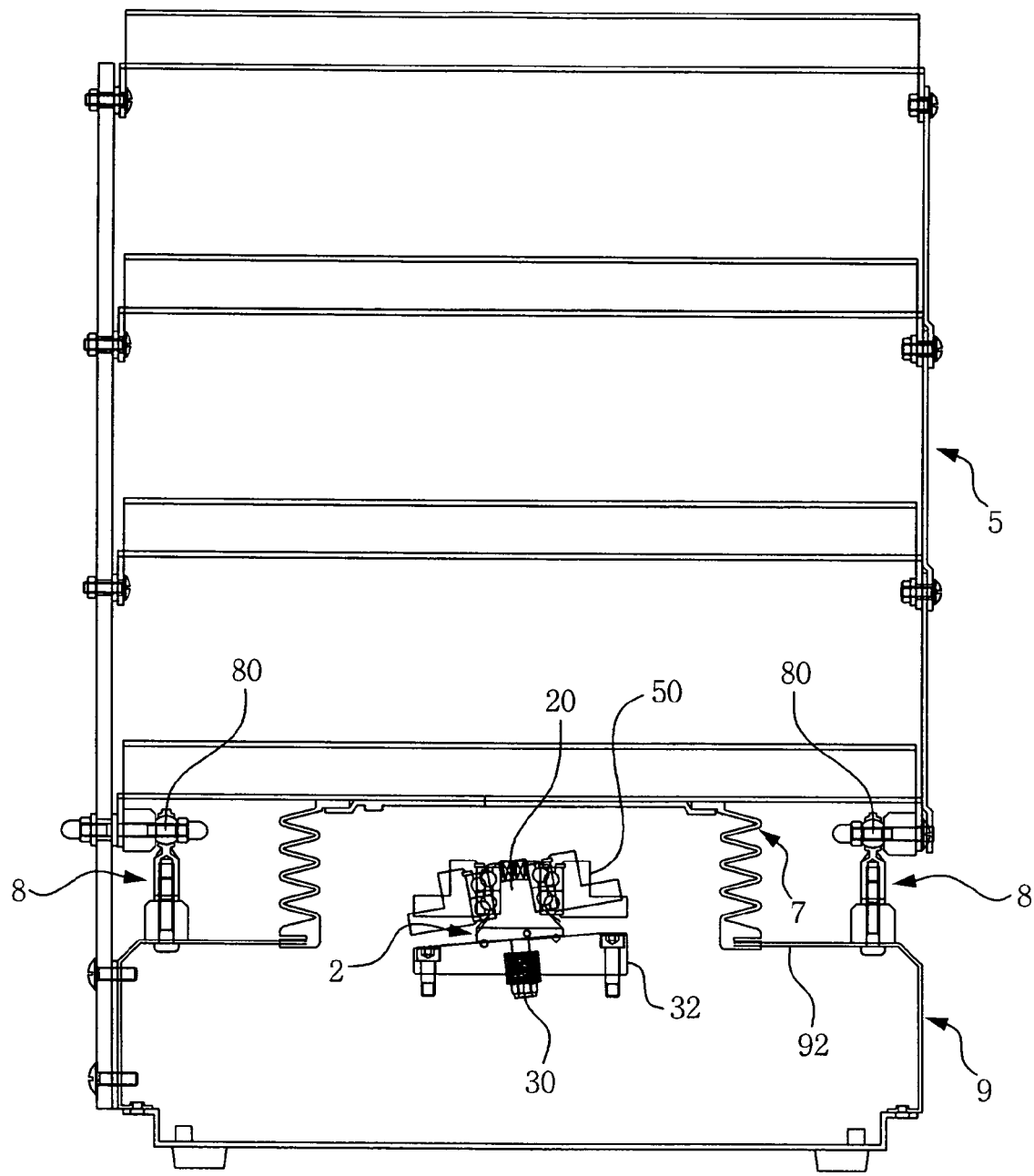
FIG. 12 is a longitudinally cross-sectional view of an experimental mixing device in accordance with another embodiment of the present invention.
Figure 13:
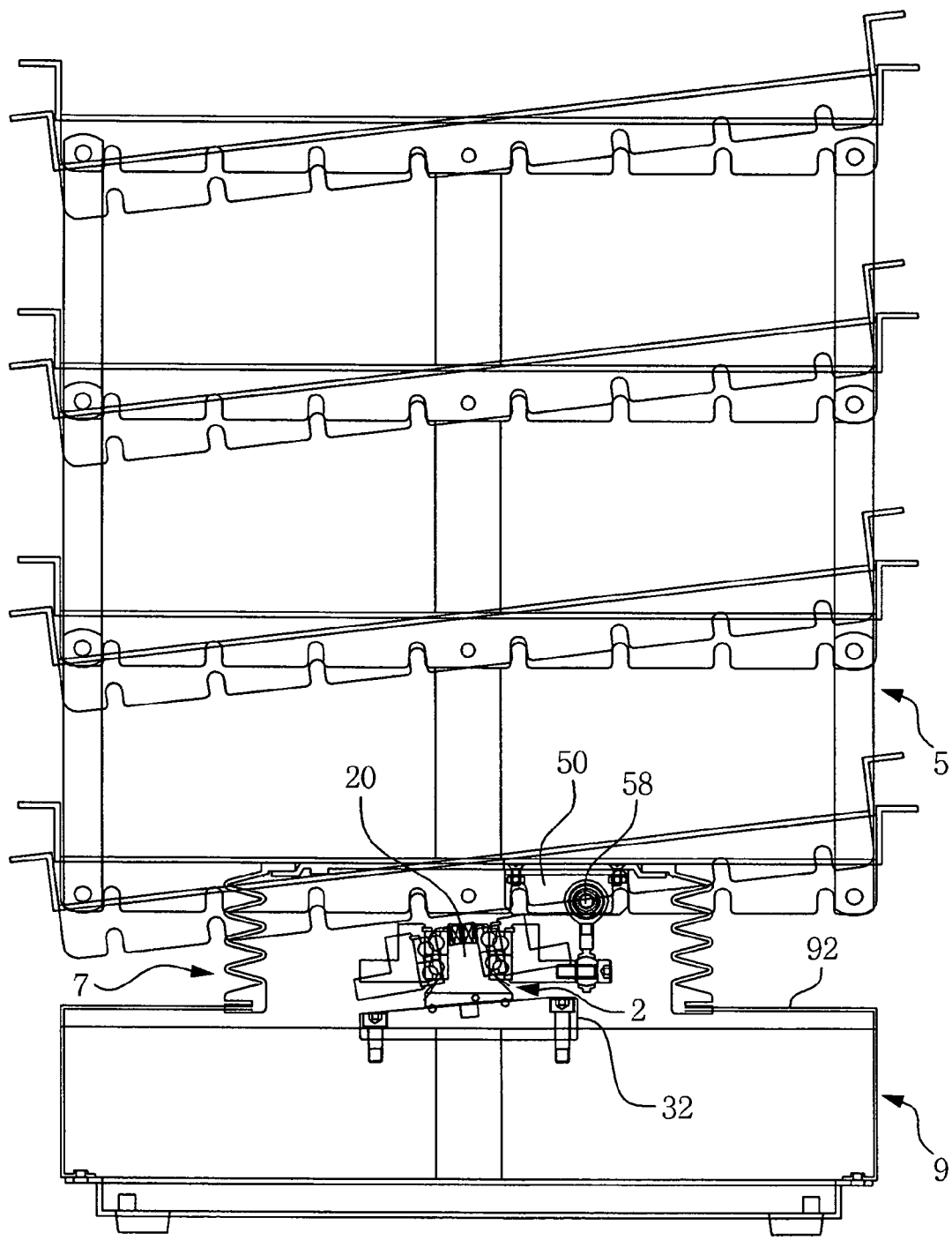
FIG. 13 is a partial side view of FIG. 12.

FIG. 12 is a longitudinally cross-sectional view of an experimental mixing device in accordance with another embodiment of the present invention. FIG. 13 is a partial side view of FIG. 12.

Referring to FIGS. 12 and 13, the mixing device may comprise a multiple mixing member 5. Each mixing member 5 may be connected to each other using a four-bar linkage to simultaneously provide mixing motions each mixing member 5. Variations and/or modifications may be applied to components other than the mixing member 5, for example a driving source 1, an eccentric member 2, a control member 3, a support member 7 or a base 9.

Figure 14:
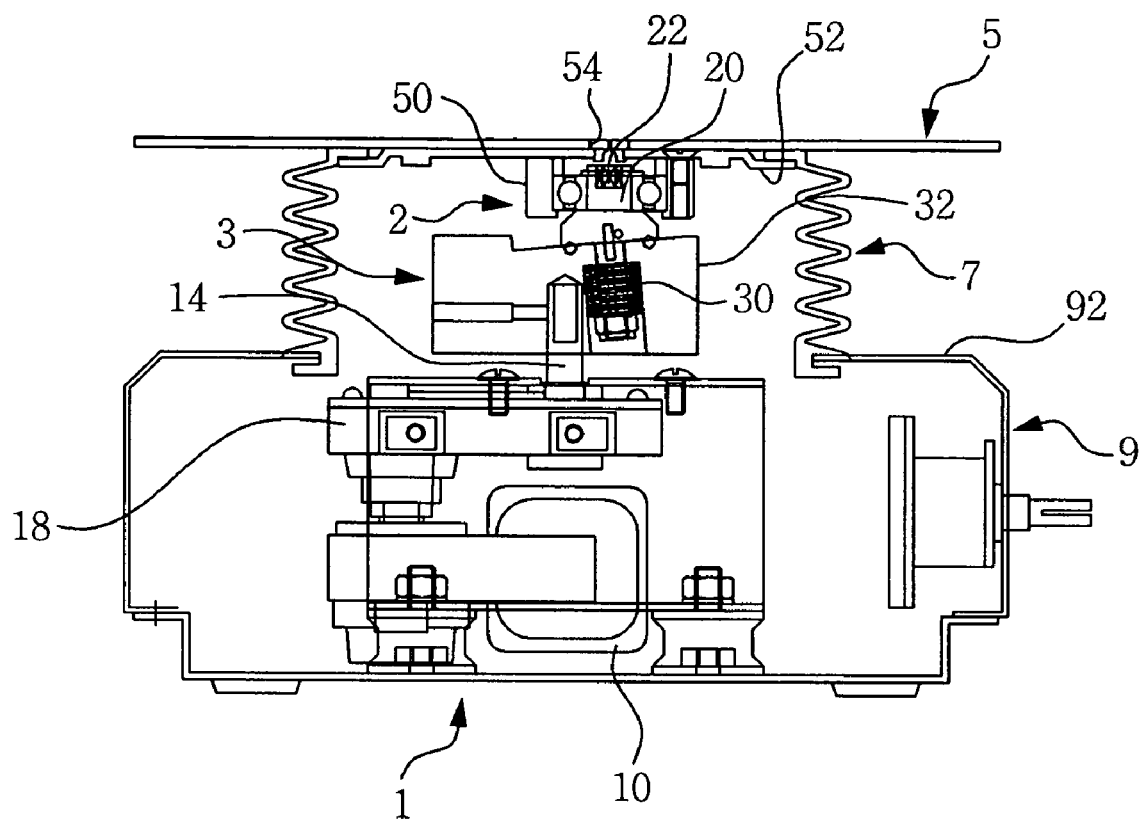
FIG. 14 is a longitudinally cross-sectional view of an experimental mixing device in accordance with another embodiment of the present invention.

FIG. 14 is a longitudinally cross-sectional view of an experimental mixing device in accordance with another embodiment of the present invention.

Referring to FIG. 14, the mixing device may further comprise a decelerator 18 to reduce the speed of a secondary axle 14. A driving source 1 may be transmitted to the secondary axle 14 from a driving motor 10 through the decelerator 18.

Figure 15:
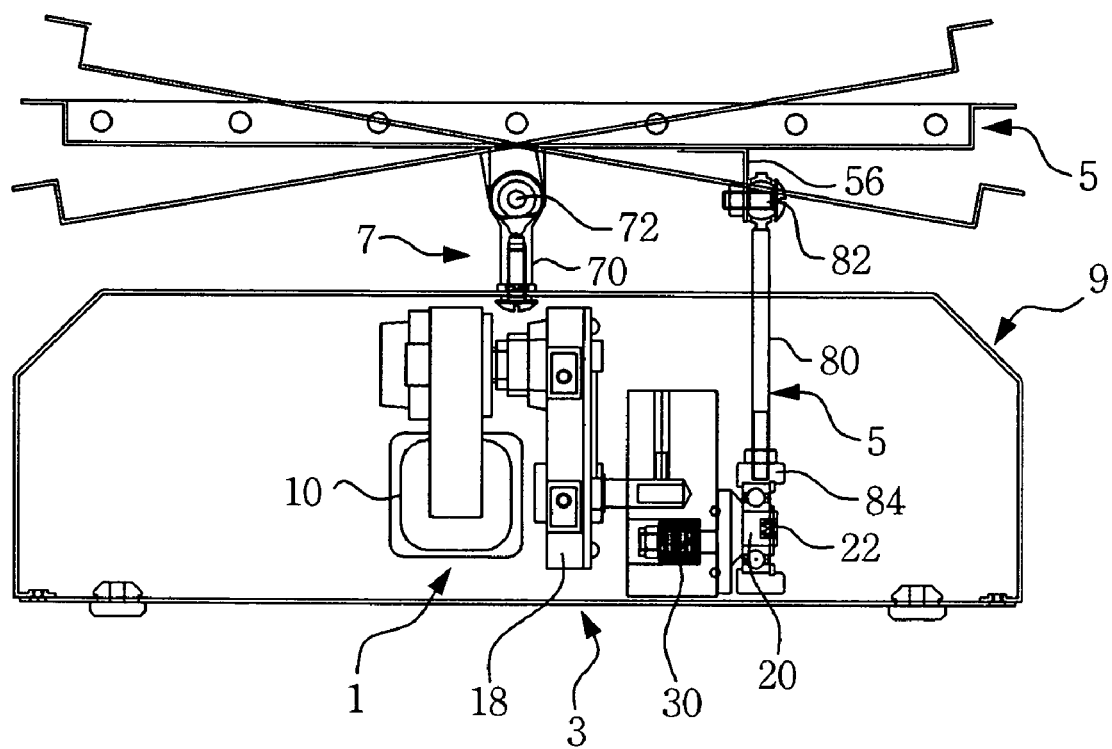
FIG. 15 is a longitudinally cross-sectional view of an experimental mixing device in accordance with another embodiment of the present invention.

FIG. 15 is a longitudinally cross-sectional view of an experimental mixing device in accordance with another embodiment of the present invention.

Referring to FIG. 15, the mixing device may further comprise a hinge member 70 having a hinge portion 72. A support member 7 may be connected to a base 9 by the hinge member 70. A secondary axle 14 of a driving source 1 may be arranged at a horizontal position. An eccentric member 2 and a control member 3 may be connected in the secondary axle 14. A connection member 8 may be provided between an eccentric axle 20 of the eccentric member 2 and the bottom of the mixing member 5. As the eccentric axle 20 may be adjusted by the eccentric rotation of the eccentric member 2, the mixing member 5 may make a see-saw motion relative to the hinge portion 72 of the hinge member 70.

The mixing member 5 may have a fixing bracket 56 connected to the top of the connection member 8 by a hinged portion 82. The connection member 8 may have an axle support 84 formed on the bottom thereof, which may be connected to the eccentric axle 20.

Figure 16:
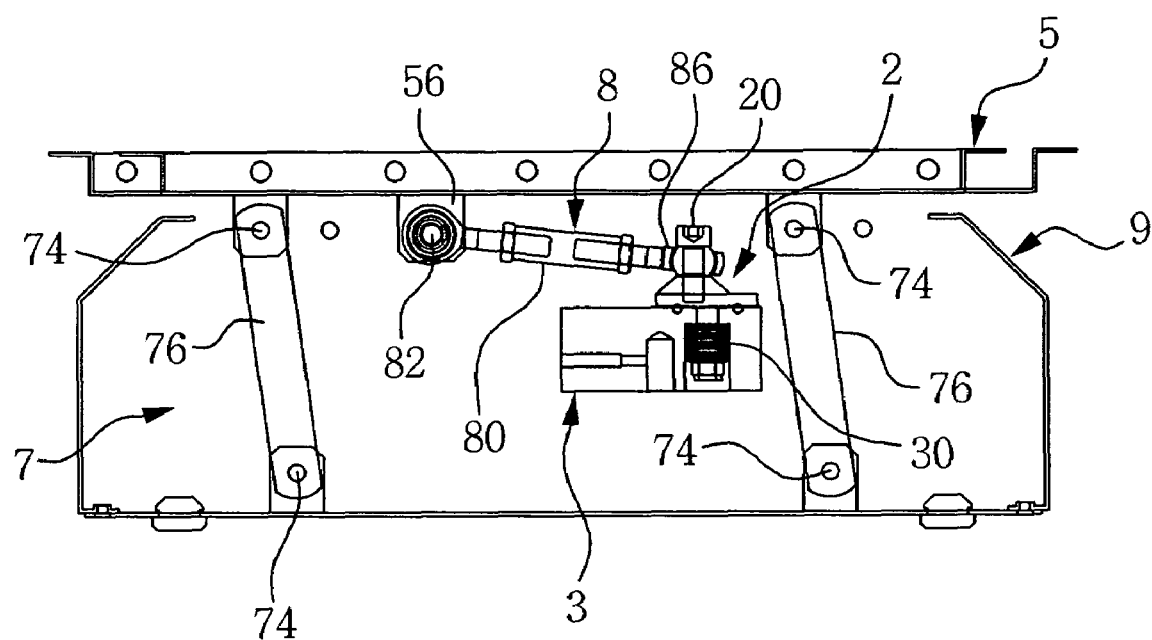
FIG. 16 is a longitudinally cross-sectional view of an experimental mixing device in accordance with another embodiment of the present invention.

FIG. 16 is a longitudinally cross-sectional view of an experimental mixing device in accordance with another embodiment of the present invention.

Referring to FIG. 16, a support member 7 may be connected to a base 9 using a four-bar linkage 76 having hinge portions 74. An eccentric member 2 and a control member 3 may be horizontally arranged in an eccentric axle 14 of a driving source 1. A connection member 8 may be the provided between an eccentric axle 20 of the eccentric member 2 and the four-bar linkage 76 of the support member 7. As the eccentric axle 20 may be adjusted by the eccentric rotation of the eccentric member 2, the mixing member 5 may make a horizontal crank motion relative to the hinge portions 74.

One end of the hinge member 80 may be connected to a fixing bracket 56 of the mixing member 5 by a hinged portion 82. The other end of the hinge member 80 may have a ball joint 86 connected to the eccentric axle 20.

Reference numeral 4 is a balance weight.

The operation of the experimental mixing device of the present invention is described blow.

A driving motor 10 as a driving source 1 may be operated to rotate a longitudinal concentric axle 14 using a driving axle 12, a driving pulley 13, a belt 16 and a secondary pulley 15, or using a decelerator 18. An eccentric member 2 connected to the secondary axle 14 may be rotated with the rotation of the secondary axle 14. As the eccentric member 2 may be rotated, an eccentric axle 20 provided on the eccentric member 2 may be rotated. A mixing member 5 connected to the eccentric axle 20 may make an orbital motion.

Specifically, as shown in FIGS. 1 and 2, an eccentric member 2 may be directly connected to a secondary pulley 15 without a control member. As an eccentric axle 20 of the eccentric member 2 may be eccentrically rotated by a driving source 1, a mixing member 5 may make a two-dimensional orbital motion.

As shown in FIGS. 3 through 5, a mixing device may further comprise a control member 3. The control member 3 may be configured to control the eccentric distance of an eccentric axle 20 between the axial center of a secondary axle 14 and the axial center of the eccentric axle 20, thereby adjusting the diameter of the orbital motion.

A knob 90 may be provided to prevent a simultaneous rotation of a secondary axle 14 with the rotation of the eccentric axle 20. When pressure may be applied to the knob 90, the front end of the knob 90 may be inserted in a slot 15a. Thereby, the secondary axle 14 may be fixed. With the secondary axle 14 being fixed, the eccentric axle 20 may be rotated, and accordingly the eccentric member 2 may be rotated relative to a control eccentric axle 30. Stopper protrusions 44 may be engaged with stopper grooves 42 to fix the eccentric member 2 at a desired position. Therefore, the eccentric distance may be controlled to adjust the diameter of the orbital motion.

As the eccentric axle 20 of the eccentric member 2 may be eccentrically rotated by the driving source 1, the mixing member 5 may make a two-dimensional orbital motion.

As shown in FIGS. 6 through 8, a knob 90 may be provided in a bracket 94 and be supported by a spring 96. When pressure may be applied to the knob 90, the front end of the knob 90 may be inserted in a slot 15a. Thereby a secondary axle 14 may be fixed. With the secondary axle 14 being fixed, an eccentric axle 20 may be rotated using a multilateral groove 22. A stopper 45 may be inserted in a stopper groove 43 to fix the eccentric member 2 at a desired position. Therefore the eccentric distance may be controlled to adjust the diameter of the orbital motion.

As the eccentric axle 20 of the eccentric member 2 may be eccentrically rotated by a driving source 1, a mixing member 5 may make a two-dimensional orbital motion.

As shown in FIGS. 9 and 10, an arm 32 may have the top surface formed tilted or a recess 46 of an arm 32 may be formed tilted. Thereby an eccentric member 2 may be arranged tilted relative to a control eccentric axle 32. Therefore, the eccentric distance and the tilt angle of the eccentric axle 20 may be simultaneously adjusted to provide a mixing member 5 with various operational motions, for example a two-dimensional horizontal orbital motion or a three-dimensional twist motion.

As shown in FIG. 11, a mixing device may further comprise a connecting element 58 and a connection member 8. The connecting element 58 may have hinged portions 80 arranged at the bottom ends of a mixing member 5 corresponding to a base 9. As an eccentric member 2 may be rotated, the mixing member 5 may make a see-saw motion relative to the hinged portions 80.

As shown in FIGS. 12 and 13, a mixing device may comprise a multiple mixing member 5 of a four-bar linkage type. Each mixing member 5 may be connected to each other using a four-bar linkage, thereby simultaneously providing operational motions each mixing member 5.

As shown in FIG. 15, a mixing device may comprise a hinge member 70 having a hinge portion 72. As an eccentric axle 20 may be rotated, a mixing member 5 may make a see-saw motion relative to the hinge portion 72.

As shown in FIG. 16, a mixing device may comprise a four-bar linkage 76 having hinged portions 74. As an eccentric axle 20 may be rotated, a mixing member 5 may make a crank motion relative to the hinged portions 74.

In accordance with the example embodiments of the present invention, the mixing device may comprise a control member selectively installed therein. The control member may adjust the eccentric distance or the tilt angle of an eccentric axle of an eccentric member so as to control a mixing member. Thereby the mixing member may provide various operational motions according to experimental requirements, for example an orbital motion, a see-saw motion, a 3-D twist motion, or a crank motion. The patterns and quantity of the operational motion of the mixing member may be also adjustable. The use of the control member may eliminate the need of separating the mixing member from the experimental mixing device. Further, the experimental mixing device may be easily used and manufactured.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. An experimental mixing device comprising:
a driving source including a driving motor;
an eccentric member having a central axis, said eccentric member including a base portion and an eccentric axle having an eccentric axis which is eccentric with the central axis;
a secondary axle rotatable about a drive axis, the secondary axle being drivably connected to the driving source so as to be rotatably driveable by the driving source, said base portion of said eccentric member being mountable in a fixed mounting position at an upper portion of said secondary axle while oriented in selectively different circumferential positions relative to the secondary axle so as to be non-rotatable with respect to said secondary drive axle when mountably received in a respective one of said different circumferentially oriented positions, said central axis being eccentric with said drive axis when said eccentric member is mounted in said fixed mounting position;
a mixing member configured to perform a mixing operation;
a support member provided below the mixing member and configured to support the mixing member;
a base provided below the support member and configured to enclose the driving source; and
a control device which is positionally interposed between the eccentric member and the secondary axle, said control device including an arm, the eccentric member being mountably receivable on the arm, rotation of the eccentric axle adjusts a tilt angle of the eccentric member.

2. An experimental mixing device comprising:
a driving source including a driving motor;
an eccentric member having a central axis, said eccentric member including a base portion and an eccentric axle having an eccentric axis which is eccentric with the central axis;
a secondary axle rotatable about a drive axis, the secondary axle being drivably connected to the driving source so as to be rotatably driveable by the driving source, said base portion of said eccentric member being mountable in a fixed mounting position at an upper portion of said secondary axle while oriented in selectively different circumferential positions relative to the secondary axle so as to be non-rotatable with respect to said secondary drive axle when mountably received in a respective one of said different circumferentially oriented positions, said central axis being eccentric with said drive axis when said eccentric member is mounted in said fixed mounting position;
a mixing member configured to perform a mixing operation;
a support member provided below the mixing member and configured to support the mixing member;
a base provided below the support member and configured to enclose the driving source; and
a control device which is positionally interposed between the eccentric member and the secondary axle, said control device including an arm, the eccentric member being mountably receivable on the arm, rotation of the eccentric axle adjusts a tilt angle of the eccentric member, and further including
a control eccentric axle carried below the eccentric member and formed eccentric with the eccentric axle,
an installation hole formed in the arm and eccentric with the secondary axle, through which the control eccentric axle passes,
a spring and a nut, with which the control eccentric axle is joined, and
the eccentric member has a plurality of stopper grooves arranged radially and the arm has a plurality of stopper protrusions corresponding to the stopper grooves to cooperatively maintain said eccentric member nonrotatable with respect to said secondary drive axle when mountably received in a respective one of said different circumferentially oriented positions.

3. An experimental mixing device comprising:
a driving source including a driving motor;
an eccentric member having a central axis, said eccentric member including a base portion and an eccentric axle having an eccentric axis which is eccentric with the central axis;

a secondary axle rotatable about a drive axis, the secondary axle being drivably connected to the driving source so as to be rotatably driveable by the driving source, said base portion of said eccentric member being mountable in a fixed mounting position at an upper portion of said secondary axle while oriented in selectively different circumferential positions relative to the secondary axle so as to be non-rotatable with respect to said secondary drive axle when mountably received in a respective one of said different circumferentially oriented positions, said central axis being eccentric with said drive axis when said eccentric member is mounted in said fixed mounting position;

a mixing member configured to perform a mixing operation;

a support member provided below the mixing member and configured to support the mixing member;

a base provided below the support member and configured to enclose the driving source; and a control device which is positionally interposed between the eccentric member and the secondary axle, said control device including an arm having a top surface which is tilted relative to said drive axis, a bottom facing surface of said base portion being tilted with respect to said eccentric axis so that the eccentric member is adjusted to selectively provide an operational motion of the mixing member by a different degree of tilting of the eccentric axis dependent upon mounting of the eccentric member in a particular respective one of said different circumferentially oriented positions.

* * * * *